US006692764B2

(12) United States Patent
Katdare et al.

(10) Patent No.: US 6,692,764 B2
(45) Date of Patent: Feb. 17, 2004

(54) WET GRANULATION FORMULATION FOR BISPHOSPHONIC ACIDS

(75) Inventors: Ashok V. Katdare, Norristown, PA (US); Kenneth A. Kramer, Green Lane, PA (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 10/252,755

(22) Filed: Sep. 23, 2002

(65) Prior Publication Data

US 2003/0032628 A1 Feb. 13, 2003

Related U.S. Application Data

(63) Continuation of application No. 10/090,541, filed on Mar. 4, 2002, now abandoned, which is a continuation of application No. 09/783,833, filed on Feb. 15, 2001, now abandoned, which is a continuation of application No. 09/099,828, filed on Jun. 18, 1998, now abandoned, which is a continuation of application No. 09/236,904, filed on Apr. 29, 1994, now abandoned.

(51) Int. Cl.[7] .......................... A61K 9/20; A61K 31/66; C07F 9/22
(52) U.S. Cl. ....................... 424/465; 424/469; 424/470; 514/108; 514/114; 514/210; 562/13; 562/14; 562/18
(58) Field of Search .............................. 562/13, 14, 18; 514/210, 108, 114; 424/465, 469, 470

(56) References Cited

U.S. PATENT DOCUMENTS

| | | | | |
|---|---|---|---|---|
| 3,962,432 A | * | 6/1976 | Schmidt-Dünker | .......... 514/108 |
| 4,054,598 A | * | 10/1977 | Blum et al. | .................... 562/13 |
| 4,134,969 A | * | 1/1979 | Schmidt-Deünker | .......... 424/49 |
| 4,267,108 A | * | 5/1981 | Blum et al. | .................. 548/413 |
| 4,327,039 A | * | 4/1982 | Blum et al. | .................... 562/13 |
| 4,407,761 A | * | 10/1983 | Blum et al. | .................... 562/13 |
| 4,578,376 A | * | 3/1986 | Rosini | ......................... 514/108 |
| 4,621,077 A | * | 11/1986 | Rosini et al. | ............... 514/108 |
| 4,624,947 A | * | 11/1986 | Blum et al. | .................. 514/108 |
| 4,639,338 A | | 1/1987 | Stahl et al. | |
| 4,639,458 A | | 1/1987 | Katdare | |
| 4,711,880 A | | 12/1987 | Stahl et al. | |
| 4,746,654 A | * | 5/1988 | Breliere et al. | ............. 514/108 |
| 4,898,736 A | | 2/1990 | Katdare | |
| 4,910,022 A | | 3/1990 | Bavitz et al. | |
| 4,922,007 A | * | 5/1990 | Kieczykowski et al. | ....... 562/13 |
| 4,942,157 A | | 7/1990 | Gall et al. | |
| 4,980,171 A | * | 12/1990 | Fels et al. | .................... 424/473 |
| 5,041,428 A | | 8/1991 | Isomura et al. | |
| 5,096,717 A | | 3/1992 | Wirth et al. | |
| 5,344,825 A | | 9/1994 | Khanna et al. | |
| 5,356,887 A | | 10/1994 | Brenner et al. | |
| 5,358,941 A | | 10/1994 | Bechard et al. | |

FOREIGN PATENT DOCUMENTS

| | | | |
|---|---|---|---|
| DE | 2 130 794 | * | 1/1973 |
| EP | 039 033 A1 | * | 11/1981 |
| EP | 100 718 A1 | * | 5/1984 |
| EP | 162 510 A1 | * | 11/1985 |
| EP | 0 177 443 A1 | | 4/1986 |
| EP | 186 405 A2 | * | 7/1986 |
| EP | 203 649 A2 | * | 12/1986 |
| EP | 252 504 A1 | * | 1/1988 |
| EP | 0 282 320 A1 | | 9/1988 |
| EP | 0 336 851 A1 | | 10/1989 |
| EP | 0 421 921 A1 | | 4/1991 |
| EP | 0 566 535 A1 | | 10/1993 |
| EP | 0 623 347 A1 | | 11/1994 |
| FR | 2 259 615 | | 8/1975 |
| FR | 2 252 223 | * | 10/1983 |
| FR | 2 531 088 | * | 2/1984 |
| WO | W O 86/00902 A1 | * | 2/1986 |
| WO | W O 87/03598 A1 | * | 6/1987 |
| WO | WO 92/11269 | | 7/1992 |
| WO | WO 93/21907 | | 11/1993 |
| WO | WO 94/12200 | | 6/1994 |

OTHER PUBLICATIONS

Gennaro et al. (I) (eds.), *Remington's Pharmaceutical Sciences, 18th Ed.*, Mack Publishing Co.(Easton, PA), 1990, pp. 1635–1645.*
Gennaro et al. (II) (eds.), *Remington's Pharmaceutical Sciences, 18th Ed.*, Mack Publishing Co.(Easton, PA), 1990, pp. 1646–1665.*
Wade et al. (I) (eds.), "Carboxymethylcellulose Sodium," in *Handbook of Pharma. Excipients, 2nd Ed.*, Am Pharm. Assoc., Washington, DC, 1994, pp. 78–81.*
Wade et al. (II) (eds.), "Microcrystalline Cellulose," in *Handbook of Pharmaceutical Excipients, 2nd Ed.*, Am Pharmaceutical Assoc., Washington, DC, 1994, pp. 84–87.*
Wade et al. (III) (eds.), "Powdered Cellulose," in *Handbook of Pharmaceutical Excipients, 2nd Ed.*, Am Pharmaceutical Assoc., Washington, DC, 1994, pp. 88–90.*
Wade et al. (IV) (eds.), "Lactose," in *Handbook of Pharmaceutical Excipients, 2nd Ed.*, Am Pharmaceutical Assoc., Washington, DC, 1994, pp. 252–260.*
Wade et al. (V) (eds.), "Pregelatinized Starch," in *Handbook of Pharmaceutical Excipients, 2nd Ed.*, Am Pharmaceutical Assoc., Washington, DC, 1994, pp. 491–493.*
Ash et al. (eds.), *Handbook of Pharmaceutical Additives*, Gower(publisher), 1995, pp. 396–397, 575, 624 and 796.*

(List continued on next page.)

*Primary Examiner*—James O. Wilson
*Assistant Examiner*—Lawrence E Crane
(74) *Attorney, Agent, or Firm*—Nicole M. Beeler; J. Antonio Garcia-Rivas; Mark R. Daniel

(57) ABSTRACT

Pharmaceutical compositions of bisphosphonic acids, and salts thereof, are prepared by wet granulation tablet formulation. These pharmaceutical compositions are useful in the treatment of disturbances involving calcium or phosphate metabolism, in particular, the treatment and prevention of diseases involving bone resorption, especially osteoporosis, Paget's disease, malignant hypercalcemia, and metastatic bone disease. These compositions are prepared without the addition of binder; instead, the drug itself acts as a binder.

15 Claims, No Drawings

OTHER PUBLICATIONS

Marshall et al., "Tablet Dosage Forms," in *Modern Pharmaceutics*, Marcel Dekker, Inc., New York, NY, 1990, only pp. 372–375 supplied.*

Rudnic et al., "Oral Solid Dosage Forms," Ch. 89 in *Remington's Pharmaceutical Sciences*, Gennaro et al. (eds.), Mack Publishing Co., Easton, PA, 1990, pp. 1633–1636, see pp. 1635–1636 in particular.*

Reynolds et al.(eds.), *Martindale—The Extra Pharmacopoeia, 30th Edition*, The Pharmaceutical Press, London, GB, 1993, p. 1218, cols. 1–2.*

The Committee of Revision, *The National Formulary, The United States Pharmacopeia*, United States Pharmacopeial Convention (Bd of Trustees), Rockville, MD, Jan. 1, 1995; only title page and text p. 2238 supplied.*

* cited by examiner

WET GRANULATION FORMULATION FOR BISPHOSPHONIC ACIDS

RELATED APPLICATIONS

This application is a continuation of Ser. No. 10/090,541, filed Mar. 4, 2002 now abandoned, which is a continuation of U.S. application Ser. No. 09/783,833 now abandoned, filed Feb. 15, 2001, which is a continuation of a twice filed continuing prosecution U.S. application Ser. No. 09/099,828 now abandoned, filed Jun. 18, 1998, which in turn is a continuation of U.S. application Ser. No. 09/236,904, filed Apr. 29, 1994, now abandoned.

BACKGROUND OF THE INVENTION

The pharmaceutical industry employs various methods for compounding pharmaceutical agents in tablet formulations. In particular, wet granulation is one of the most prevalent methods. Tablets prepared by wet granulation generally require the addition of a binding agent to keep the tablet together.

A variety of bisphosphonic acids have been disclosed as being useful in the treatment and prevention of diseases involving bone resorption. Representative examples may be found in the following:

U.S. Pat. No. 3,962,432; U.S. Pat. No. 4,054,598;

U.S. Pat. No. 4,267,108; U.S. Pat. No. 4,327,039;

U.S. Pat. No. 4,621,077; U.S. Pat. No. 4,624,947;

U.S. Pat. No. 4,746,654; U.S. Pat. No. 4,922,077; and EPO Patent Pub. No. 0,252,504. Standard methods for tablet formulation of bisphosphonic acids, however, suffer difficulties.

Wet granulated formulations need to have an agent called a "binder," which, in contact with water, swells or starts dissolving, forming a gel-like consistency. Traditionally, starch, starch paste, gelatin, and cellulosics such as hydroxypropylmethyl cellulose, hydroxyethyl cellulose, hydroxypropyl cellulose, polyvinyl pyrrolidone are used as binding agents in wet granulation formulations. (See, Remington's Pharmaceutical Sciences, 18th ed, (Mack Publishing Company: Easton, Pa., 1990), pp. 1635–36). Microcrystalline cellulose, such as Avicel PH101, may be employed as a binder or compression aid in compositions prepared by dry granulation formulation, but microcrystalline cellulose functions primarily as a bulking agent in wet granulation formulations because the microcrystalline cellulose loses much of its binding properties upon wetting.

The wet granulation process helps to form agglomerates of powders. These agglomerates are called "granules." The present invention provides for a wet granulated formulation of bisphosphonic acids and process therefor wherein the tablet formulation does not contain any binder. Instead, the drug itself acts as a binder. The absence of a separate binder keeps the formulation simpler, and minimizes adverse effects that binding agents can have on dissolution. Elimination of binder also simplifies the optimization and characterization of the formulation.

DESCRIPTION OF THE INVENTION

The present invention is directed in a first embodiment to a process for the preparation of pharmaceutical compositions of bisphosphonic acids by wet granulation formulation. This process employs a blend of a bisphosphonic acid and minimal amounts of other processing aids with no binder added. This tablet formulation is prepared by:

(1) forming a powder blend of the active ingredient with diluents, (2) wet granulating the powder blend with water to form granules, (3) drying the granules to remove water, and (4) compressing the lubricated granule mixture into a desired tablet form.

The shape of the tablet is not critical.

More specifically, this embodiment of the present invention concerns a process for the preparation of a tablet containing a bisphosphonic acid as an active ingredient which process comprises:

(1) forming a powder blend of the active ingredient with diluents from 3 to 25 minutes using a mixer such as a planetary or high shear granulator, (2) wet granulating the powder blend by the addition of water while mixing over a 2 to 30 minute period to form granules, (3) drying the granules to remove water by the use of heated air for 10 minutes to 24 hours in a dryer (fluid bed or tray type), (4) milling the dried granules to a uniform size, (5) adding and blending a disintegrant with the dried milled particles for 2 to 30 minutes, (6) adding and blending a lubricant to the mixture containing the disintegrant for 30 seconds to 20 minutes, and (7) compressing the lubricated granule mixture into a desired tablet form.

One particularly preferred process employs a high shear granulator as a mixer and comprises the steps of:

(1) forming a powder blend of 4-amino-1-hydroxybutylidene-1,1-bisphosphonic acid, microcrystalline cellulose, such as Avicel PH101, and lactose with a high shear granulator for 3 to 5 minutes, (2) wet granulating the powder blend by the addition of water while mixing over a 3 to 5 minute period to form granules with the high shear granulator, (3) drying the granules to remove water by the use of heated air by drying 10 minutes to 1 hour with a fluid bed, or 12–24 hours in a tray dryer, preferably with a fluid bed, (4) milling the dried granules to a uniform size using a hammer type mill, (5) adding and blending the disintegrant croscarmellose sodium NF type A with the dried milled particles for 3 to 8 minutes, (6) adding and blending magnesium stearate lubricant to the mixture containing the croscarmellose sodium NF type A disintegrant with a ribbon blender or a planetary mixer for 3 to 8 minutes, and (7) compressing the lubricated granule mixture into a desired tablet form, and (8) dedusting and storing the tablets.

Another particularly preferred process employs a planetary granulator as a mixer and comprises the steps of:

(1) forming a powder blend of 4-amino-1-hydroxybutylidene-1,1-bisphosphonic acid, microcrystalline cellulose such as Avicel PH101, and lactose with a planetary granulator for 10 to 25 minutes, (2) wet granulating the powder blend by the addition of water while mixing over a 3 to 10 minute period to form granules with the planetary granulator, (3) drying the granules to remove water by the use of heated air by drying 10 minutes to 1 hour with a fluid bed, or 12–24 hours in a tray dryer, preferably with a fluid bed, (4) milling the dried granules to a uniform size using a hammer type mill, (5) adding and blending the disintegrant croscarmellose sodium NF type A with the dried milled particles for 3 to 8 minutes, (6) adding and blending magnesium stearate lubricant to the mixture containing the croscarmellose sodium NF type A disintegrant with a ribbon blender or a planetary granulator for 3 to 8 minutes, and (7) compressing the lubricated granule mixture into a desired tablet form, and (8) dedusting and storing the tablets.

Still another particularly preferred process employs a high shear granulator as mixer, and comprises the steps of:

(1) forming a powder blend of 4-amino-1-hydroxybutylidene-1,1-bisphosphonic acid, microcrystalline cellulose, such as Avicel PH101, and lactose with a high shear granulator for 3 to 5 minutes, (2) wet granulating the powder blend by the addition of water while mixing over a 3 to 5 minute period to form granules with a high shear granulator, (3) drying the granules to remove water by the use of heated air for 10 minutes to one hour using a fluid bed dryer, (4) milling the dried granules to a uniform size using a hammer type mill, (5) adding and blending the disintegrant croscarmellose sodium NF type A with the dried milled particles for 3 to 8 minutes, (6) adding and blending magnesium stearate lubricant to the mixture containing the croscarmellose sodium NF type A disintegrant with a ribbon blender for 3 to 8 minutes, (7) compressing the lubricated granule mixture into a desired tablet form, and (8) dedusting and storing the tablets.

Granulation is the process of adding water to a powder mixture with mixing until granules are formed. The granulation step may be varied from 2 to 30 minutes, preferably 2 to 5 minutes. The lubrication step is the process of adding lubricant to the mixture; the lubrication step may be varied from 30 seconds to 20 minutes, preferably 3 to 8 minutes.

The disclosed process may be used to prepare solid dosage forms, particularly tablets, for medicinal administration.

Preferred diluents include: lactose, microcrystalline cellulose, calcium phosphate(s), mannitol, powdered cellulose, pregelatinized starch, and other suitable diluents. Especially preferred are lactose and microcrystalline cellulose. In particular, microcrystallione cellulose NF, especially Avicel PH101, the trademarked name for microcrystalline cellulose NF manufactured by FMC Corp. is preferred.

The disintegrant may be one of several modified starches or modified cellulose polymers, in particular, croscarmellose sodium is preferred. Croscarmellose sodium NF Type A is commercially available under the trade name "Ac-di-sol".

Preferred lubricants include magnesium stearate, calcium stearate, stearic acid, surface active agents such as sodium lauryl sulfate, propylene glycol, sodium dodecane sulfonate, sodium oleate sulfonate, and sodium laurate mixed with stearates and talc, sodium stearyl fumerate, and other known lubricants. Especially preferred is magnesium stearate.

Examples of the bisphosphonic acids which may be employed as active ingredients in the instant invention include:

(a) 4-amino-1-hydroxybutylidene-1,1-bisphosphonic acid;

(b) N-methyl-4-amino-1-hydroxybutylidene-1,1-bisphosphonic acid;

(c) 4-(N,N-dimethylamino)-1-hydroxybutylidene-1,1-bisphosphonic acid;

(d) 3-amino-1-hydroxypropylidene-1,1-bisphosphonic acid;

(e) 3-(N,N-dimethylamino)-1-hydroxypropylidene-1,1-bisphosphonic acid;

(f) 1-hydroxy-3-(N-methyl-N-pentylamino)propylidene-1,1-bisphosphonic acid;

(g) 1-hydroxy-2-[3-pyridyl]ethylidene-1,1-bisphosphonic acid; and (h) 4-(hydroxymethylene-1,1-bisphosphonic acid)-piperidine; or pharmaceutically acceptable salts thereof.

Methods for the preparation of bisphosphonic acids may be found in, e.g., U.S. Pat. No. 3,962,432; U.S. Pat. No. 4,054,598; U.S. Pat. No. 4,267,108; U.S. Pat. No. 4,327,039; U.S. Pat. No. 4,407,761; U.S. Pat. No. 4,621,077; U.S. Pat. No. 4,624,947; U.S. Pat. No. 4,746,654; U.S. Pat. No. 4,922,077; and EPO Patent Pub. No. 0,252,504. In particular, methods for the preparation of 4-amino-1-hydroxy-butylidene-1,1-bisphosphonic acid and 4-amino-1-hydroxy-butylidene-1,1-bisphosphonic acid monosodium salt trihydrate may be found in U.S. Pat. No. 4,407,761 and U.S. Pat. No. 4,922,077, respectively.

The pharmaceutically acceptable salts of bisphosphonic acids may also be employed in the instant invention. Examples of base salts of bisphosphonic acids include ammonium salts, alkali metal salts such as potassium and sodium (including mono-, di- and tri-sodium) salts (which are preferred), alkaline earth metal salts such as calcium and magnesium salts, salts with organic bases such as dicyclohexylamine salts, N-methyl-D-glucamine, and salts with amino acids such as arginine, lysine, and so forth. The non-toxic, physiologically acceptable salts are preferred. The salts may be prepared by methods known in the art, such as in U.S. Pat. No. 4,922,077.

In the present invention it is preferred that the bisphosphonic acid is 4-amino-1-hydroxybutylidene-1,1-bisphosphonic acid. It is even more preferred that the bisphosphonic acid is a sodium salt of 4-amino-1-hydroxybutylidene-1,1-bisphosphonic acid, in particular, 4-amino-1-hydroxybutylidene-1,1-bisphosphonic acid monosodium salt trihydrate.

Preferred pharmaceutical compositions comprise about 0.5 to 40% by weight of a bisphosphonic acid as an active ingredient; about 10 to 80% by weight of anhydrous lactose or hydrous fast flow lactose; about 5 to 50% by weight of microcrystalline cellulose; and about 0.1 to 5% by weight of magnesium stearate.

The preferred pharmaceutical compositions are generally in the form of tablets. The tablets may be, for example, from 50 mg to 1.0 g in net weight, more preferably 100 to 500 mg net weight, and even more preferably 150 to 300 mg net weight.

More preferred pharmaceutical compositions in accordance with the present invention comprise: about 0.5 to 25% by weight of a bisphosphonic acid selected from 4-amino-1-hydroxybutylidene-1,1-bisphosphonic acid and 4-amino-1-hydroxybutylidene-1,1-bisphosphonic acid monosodium salt trihydrate; about 30 to 70% by weight of anhydrous lactose or hydrous fast flow lactose; about 30 to 50% by weight of microcrystalline cellulose; about 0.1 to 2% by weight of magnesium stearate; and about 0.5 to 2% by weight of a disintegrant such as croscarmellose sodium.

Especially preferred pharmaceutical compositions comprise about 1 to 25% of the active ingredient, about 40 to 60% by weight of anhydrous lactose; about 35 to 45% by weight of microcrystalline cellulose; about 0.5 to 2% by weight of croscarmellose sodium; and about 0.1 to 1% by weight of magnesium stearate. Preferred pharmaceutical compositions as envisioned for commercial development are as follows.

Tablets of 2.5 mg potency free acid:
about 1.63% by weight of 4-amino-1-hydroxybutylidene-1,1-bisphosphonic acid monosodium salt trihydrate; about 56.87% by weight of anhydrous lactose; about 40% by weight of microcrystalline cellulose; about 1% by weight of croscarmellose sodium; and about 0.5% by weight of magnesium stearate.

Tablets of 5 mg potency free acid:
about 3.25% by weight of 4-amino-1-hydroxybutylidene-1,1-bisphosphonic acid monosodium salt trihydrate; about 55.25% by weight of anhydrous lactose; about 40% by weight of microcrystalline cellulose; about 1% by weight of croscarmellose sodium; and about 0.5% by weight of magnesium stearate.

Tablets of 10 mg potency free acid:
about 6.5% by weight of 4-amino-1-hydroxy-butylidene-1,1-bisphosphonic acid monosodium salt trihydrate; about 52.0% by weight of anhydrous lactose; about 40% by weight of microcrystalline cellulose; about 1% by weight of croscarmellose sodium; and about 0.5% by weight of magnesium stearate.

Tablets of 20 mg potency free acid:
about 13.0% by weight of 4-amino-1-hydroxybutylidene-1,1-bisphosphonic acid monosodium salt trihydrate; about 45.5% by weight of anhydrous lactose; about 40% by weight of microcrystalline cellulose; about 1% by weight of croscarmellose sodium; and about 0.5% by weight of magnesium stearate.

Tablets of 40 mg potency free acid:
about 26.0% by weight of 4-amino-1-hydroxybutylidene-1,1-bisphosphonic acid monosodium salt trihydrate; about 32.5% by weight of anhydrous lactose; about 40% by weight of microcrystalline cellulose; about 1% by weight of croscarmellose sodium; and about 0.5% by weight of magnesium stearate.

Each of the tablets of the potencies above is preferably formulated in a 200 mg tablet containing 0.05 mL purified water USP per tablet.

The pharmaceutical tablet compositions of the present invention may also contain one or more additional formulation ingredients may be selected from a wide variety of excipients known in the pharmaceutical formulation art. According to the desired properties of the tablet, any number of ingredients may be selected, alone or in combination, based upon their known uses in preparing tablet compositions. Such ingredients include, but are not limited to, diluents, compression aids, disintegrants, lubricants, flavors, flavor enhancers, sweetener and preservatives. The pharmaceutical tablet compositions of the present invention do not, however, require the addition of a separate binding excipient because in wet granulation the active ingredient itself acts as a binding agent.

The term "tablet" as used herein is intended to encompass compressed pharmaceutical dosage formulations of all shapes and sizes, whether coated or uncoated. Substances which may be used for coating include hydroxypropylmethylcellulose, hydroxypropylcellulose, titanium dioxide, talc, sweeteners, and colorants.

The pharmaceutical compositions of the present invention are useful in the therapeutic or prophylactic treatment of disorders in calcium or phosphate metabolism and associated diseases. These diseases can be divided into two categories:

1. Abnormal (ectopic) depositions of calcium salts, mostly calcium phosphate, pathological hardening of tissues and bone malformations.

2. Conditions which can benefit from a reduction in bone resorption. A reduction in bone resorption should improve the balance between resorption and formation, reduce bone loss or result in bone augmentation. A reduction in bone resorption can alleviate the pain associated with osteolytic lesions and reduce the incidence and/or growth of those lesions.

These diseases include: osteoporosis (including estrogen deficiency, immobilization, glucocorticoid induced and senile), osteodystrophy, Paget's disease, myositis ossificans, Bechterew's disease, malignant hypercalcimia, metastatic bone disease, peridontal disease, cholelithiasis, nephrolithiasis, urolithiasis, urinary calculus, hardening of the arteries (sclerosis), arthritis, bursitis, neuritis and tetany.

Increased bone resorption can be accompanied by pathologically high calcium and phosphate concentrations in the plasma, which would be alleviated by use of the instant pharmaceutical compositions.

The following examples are given for the purpose of illustrating the present invention and shall not be construed as being limitations on the scope or spirit of the invention.

EXAMPLE 1

Procedure for Manufacturing 2.5 mg Potency Tablets of 4-Amino-1-hydroxybutylidene-1,1-bisphosphonic acid

| Ingredients | Per Tablet | Per 10,000 Tablets |
|---|---|---|
| Active ingredient (monosodium salt trihydrate) | 3.26 mg | 32.6 g |
| Anhydrous Lactose, NF | 113.74 mg | 1137.4 g |
| Microcrystalline Cellulose NF | 80.0 mg | 800.0 g |
| Magnesium Stearate Impalpable Powder NF | 1.00 mg | 10.0 g |
| Croscarmellose Sodium NF Type A | 2.00 mg | 20.0 g |

The active ingredient (equivalent to 2.5 mg anhydrous free acid per tablet) was mixed with the microcrystalline cellulose NF and the anhydrous lactose NF in a high shear mixer for 3 minutes. Granulating solvent (550 mL water) was added to this blend with the mixer running over a two minute period. The wetted mass was dried in a fluid bed dryer at an inlet temperature of 50° C. The dried material was then milled using a FITZPATRICK J mill (hammer-type mill) to achieve fine granules. After milling, Croscarmellose Sodium NF type A (disintegrant) was added to the blend and mixed in a ribbon blender for 5 minutes. Magnesium Stearate Impalpable Powder NF (lubricant) was added to this blend through a #60 mesh screen and blended for an additional 4 minutes. The lubricated mixture was compressed to provide tablets of 2.5 mg active ingredient.

EXAMPLE 2

Procedure for Manufacturing 10 mg Potency Tablets of 4-Amino-1-hydroxybutylidene-1,1-bisphosphonic acid

| Ingredients | Per Tablet | Per 10,000 Tablets |
|---|---|---|
| Active ingredient (monosodium salt trihydrate) | 13.05 mg | 130.5 g |
| Anhydrous Lactose, NF | 103.95 mg | 1039.5 g |
| Microcrystalline Cellulose NF | 80.0 mg | 800.0 g |
| Magnesium Stearate Impalpable Powder NF | 1.00 mg | 10.0 g |
| Croscarmellose Sodium NF Type A | 2.00 mg | 20.0 g |

Tablets were prepared using essentially the procedure of Example 1.

EXAMPLE 3

Procedure for Manufacturing 20 mg Potency Tablets of 4-Amino-1-hydroxybutylidene-1,1-bisphosphonic acid

| Ingredients | Per Tablet | Per 10,000 Tablets |
|---|---|---|
| Active ingredient (monosodium salt trihydrate) | 26.11 mg | 261.1 g |
| Anhydrous Lactose, NF | 90.89 mg | 908.9 g |
| Microcrystalline Cellulose NF | 80.0 mg | 800.0 g |
| Magnesium Stearate Impalpable Powder NF | 1.0 mg | 10.0 g |
| Croscarmellose Sodium NF Type A | 2.0 mg | 20.0 g |

Tablets were prepared using essentially the procedure of Example 1.

While the foregoing specification teaches the principles of the present invention, with examples provided for the purpose of illustration, it will be understood that the practice of the invention encompasses all of the casual variations, adaptations, modifications, deletions, or additions of procedures and protocols described herein, as come within the scope of the following claims and its equivalents.

We claim:

1. A process for the preparation of a tablet containing an active ingredient, which is the sole binder, selected from the group consisting of:
    4-amino-1-hydroxybutylidene-1,1-bisphosphonic acid;
    N-methyl-4-amino-1-hydroxybutylidene-1,1-bisphosphonic acid;
    4-(N, N-dimethylamino)-1-hydroxybutylidene-1,1-bisphosphonic acid;
    3-amino-1-hydroxypropylidene-1, 1-bisphosphonic acid;
    3-(N, N-dimethylamino)-1-hydroxypropylidene-1,1-bisphosphonic acid;
    1-hydroxy-3- (N-methyl-N-pentylamino) propylidene-1, 1-bisphosphonic acid;
    1-hydroxy-2- (3-pyridyl) ethylidene-1, 1-bisphosphonic acid; and
    4-(hydroxymethylene-1, 1-bisphosphonic acid)-piperidine; or a pharmaceutically acceptable salt thereof; which process comprises:
    (1) forming a powder blend of the active ingredient with diluents, wherein said active ingredient is the sole binder,
    (2) wet granulating the powder blend with water to form granules,
    (3) drying the granules to remove water, and
    (4) compressing the dried granules mixture into a desired tablet form.

2. The process of claim 1 wherein the active ingredient is 4-amino-1-hydroxybutylidene-1,1-bisphosphonic acid.

3. The process of claim 1 wherein the active ingredient is 4-amino-1-hydroxybutylidene-1,1-bisphosphonic acid monosodium salt trihydrate.

4. A process for the preparation of a tablet containing an active ingredient, which is the sole binder, selected from the group consisting of:
    4-amino-1-hydroxybutylidene-1,1-bisphosphonic acid;
    N-methyl-4-amino-1-hydroxybutylidene-1,1-bisphosphonic acid;
    4-(N,N-dimethylamino)-1-hydroxybutylidene-1,1-bisphosphonic acid;
    3-amino-1-hydroxypropylidene-1,1-bisphosphonic acid;
    3-(N,N-dimethylamino)-1-hydroxypropylidene-1,1-bisphosphonic acid;
    1-hydroxy-3-(N-methyl-N-pentylamino)propylidene-1,1-bisphosphonic acid;
    1-hydroxy-2-(3-pyridyl)ethylidene-1,1-bisphosphonic acid; and
    4-(hydroxymethylene-1,1-bisphosphonic acid)-piperidine; or a pharmaceutically acceptable salt thereof; which process comprises:
    (1) forming a powder blend of the active ingredient with diluents from 3 to 25 minutes using a mixer such as a planetary or high shear granulator, wherein said active ingredient is the sole binder,
    (2) wet granulating the powder blend by the addition of water while mixing over a 2 to 30 minute period to form granules,
    (3) drying the granules to remove water by the use of heated air for 10 minutes to 24 hours,
    (4) milling the dried granules to a uniform size,
    (5) adding and blending a disintegrant with the dried milled particles for 2 to 30 minutes,
    (6) adding and blending a lubricant to the mixture containing the disintegrant for 30 seconds to 20 minutes, and
    (7) compressing the dried granules mixture into a desired tablet form.

5. The process of claim 4 wherein the active ingredient is 4-amino-1-hydroxybutylidene-1,1-bisphosphonic acid.

6. The process of claim 4 wherein the active ingredient is 4-amino-1-hydroxybutylidene-1,1-bisphosphonic acid monosodium salt trihydrate.

7. The process of claim 4 wherein the diluents are selected from: lactose, microcrystalline cellulose, calcium phosphate, mannitol, powdered cellulose, and pregelatinized starch.

8. The process of claim 7 wherein the diluents are lactose and microcrystalline cellulose.

9. The process of claim 4 wherein the disintegrant is selected from the group consisting of modified starch, modified cellulose polymer, croscarmellose sodium, and a combination thereof.

10. The process of claim 9 wherein the disintegrant is croscarmellose sodium.

11. The process of claim 4 wherein the lubricant is selected from the group consisting of magnesium stearate, calcium stearate, stearic acid, sodium lauryl sulfate, propylene glycol, sodium dodecane sulfonate, sodium oleate sulfonate, sodium laurate mixed with stearates and talc, and sodium stearyl fumerate.

12. The process of claim 11 wherein the lubricant is magnesium stearate.

13. The process of claim 4 which comprises the steps:
(1) forming a powder blend of 4-amino-1-hydroxybutylidene-1,1-bisphosphonic acid, microcrystalline cellulose, and lactose with a high shear granulator for 3 to 5 minutes,
(2) wet granulating the powder blend by the addition of water while mixing over a 3 to 5 minute period to form granules with the high shear granulator,
(3) drying the granules to remove water by the use of heated air by drying 10 minutes to 1 hour with a fluid bed, or 12 to 24 hours in a tray dryer,
(4) milling the dried granules to a uniform size using a hammer type mill,
(5) adding and blending the disintegrant croscarmellose sodium with the dried milled particles for 3 to 8 minutes,
(6) adding and blending magnesium stearate lubricant to the mixture containing the croscarmellose sodium disintegrant with a ribbon blender or a planetary mixer for 3 to 8 minutes,
(7) compressing the lubricated granule mixture into a desired tablet form, and
(8) dedusting and storing the tablets.

14. The process of claim 4 which comprises the steps:
(1) forming a powder blend of 4-amino-1-hydroxybutylidene-1,1-bisphosphonic acid, microcrystalline cellulose, and lactose with a planetary granulator for 10 to 25 minutes,
(2) wet granulating the powder blend by the addition of water while mixing over a 3 to 10 minute period to form granules with the planetary granulator,
(3) drying the granules to remove water by the use of heated air by drying 10 minutes to 1 hour with a fluid bed, or 12–24 hours in a tray dryer,
(4) milling the dried granules to a uniform size using a hammer type mill,
(5) adding and blending the disintegrant croscarmellose sodium with the dried milled particles for 3 to 8 minutes,
(6) adding and blending magnesium stearate lubricant to the mixture containing the croscarmellose sodium disintegrant with a ribbon blender or a planetary granulator for 3 to 8 minutes, and
(7) compressing the lubricated granule mixture into a desired tablet form, and
(8) dedusting and storing the tablets.

15. The process of claim 4 which comprises the steps:
(1) forming a powder blend of 4-amino-1-hydroxybutylidene-1,1-bisphosphonic acid, microcrystalline cellulose, and lactose with a high shear granulator for 3 to 5 minutes,
(2) wet granulating the powder blend by the addition of water while mixing over a 3 to 5 minute period to form granules with a high shear granulator,
(3) drying the granules to remove water by the use of heated air for 10 minutes to one hour using a fluid bed dryer,
(4) milling the dried granules to a uniform size using a hammer type mill,
(5) adding and blending the disintegrant croscarmellose sodium with the dried milled particles for 3 to 8 minutes,
(6) adding and blending magnesium stearate lubricant to the mixture containing the croscarmellose sodium disintegrant with a ribbon blender for 3 to 8 minutes,
(7) compressing the lubricated granule mixture into a desired tablet form, and
(8) dedusting and storing the tablets.

* * * * *